US009616000B2

(12) United States Patent
Ishihara et al.

(10) Patent No.: US 9,616,000 B2
(45) Date of Patent: Apr. 11, 2017

(54) MEDICAL KIT AND LIQUID FILLING METHOD

(71) Applicant: TERUMO KABUSHIKI KAISHA, Shibuya-ku, Tokyo (JP)

(72) Inventors: Hiroyuki Ishihara, Kanagawa (JP); Naotaka Chino, Kanagawa (JP)

(73) Assignee: TERUMO KABUSHIKI KAISHA, Shibuya-Ku, Tokyo (JP)

(*) Notice: Subject to any disclaimer, the term of this patent is extended or adjusted under 35 U.S.C. 154(b) by 0 days.

(21) Appl. No.: 14/988,155

(22) Filed: Jan. 5, 2016

(65) Prior Publication Data

US 2016/0128905 A1 May 12, 2016

Related U.S. Application Data

(63) Continuation of application No. PCT/JP2013/068546, filed on Jul. 5, 2013.

(51) Int. Cl.

*A61B 19/00* (2006.01)
*A61J 1/20* (2006.01)
*A61J 1/22* (2006.01)

(52) U.S. Cl.

CPC ........... *A61J 1/2096* (2013.01); *A61J 1/2058* (2015.05); *A61J 1/22* (2013.01)

(58) Field of Classification Search

CPC A61J 1/2096; A61J 1/2058; A61J 1/20; A61J 1/2003; A61J 1/2089; A61J 1/22; A61J 3/00

USPC .................................................. 604/403–416

See application file for complete search history.

(56) References Cited

U.S. PATENT DOCUMENTS 4,040,420 A 8/1977 Speer
2011/0049181 A1* 3/2011 Lutz ...................... A61J 1/2096 222/137

FOREIGN PATENT DOCUMENTS

| | | | |
|---|---|---|---|
| JP | 2009-153720 A | 7/2009 |
| JP | 200915370 A | 7/2009 |
| JP | 2011-516228 A | 5/2011 |
| WO | WO 2007/101772 A1 | 9/2007 |
| WO | 2009144085 A2 | 12/2009 |

OTHER PUBLICATIONS

International Search Report (PCT/ISA/210) issued on Oct. 8, 2013, by the Japanese Patent Office as the International Searching Authority for International Application No. PCT/ JP2013/068546.
Written Opinion (PCT/ISA/237) issued on Oct. 8, 2013, by the Japanese Patent Office as the International Searching Authority for International Application No. PCT/ JP2013/068546.

* cited by examiner

*Primary Examiner* — Philip R Wiest
(74) *Attorney, Agent, or Firm* — Buchanan Ingersoll & Rooney PC

(57) ABSTRACT

A medical kit includes a liquid storage container in which a liquid is preliminarily stored, syringes, a first connector for connecting the liquid storage container and the syringes, and a regulating mechanism for collectively regulating limits of movement of gaskets of the syringes and. The syringes are collectively filled with the liquid by conducting an operation to feed out the liquid in the liquid storage container in a condition in which the liquid storage container and the syringes and in an empty state are connected through the syringes, until the limits of movement are regulated.

19 Claims, 8 Drawing Sheets

MEDICAL KIT AND LIQUID FILLING METHOD

CROSS-REFERENCES TO RELATED APPLICATIONS

This application is a continuation of International Application No. PCT/JP2013/068546 filed on Jul. 5, 2013, the entire content of which is incorporated herein by reference.

TECHNICAL FIELD

The present invention relates to a medical kit and a liquid filling method.

BACKGROUND DISCUSSION

In the medical field, in the case of drip infusion or transfusion to a patient or in the case of administering an anti-adhesion material or a biological tissue adhesive or the like to a patient, a drug may be diluted with or dissolved in a liquid and the resulting liquid medicine may be used by sucking it with a syringe. These operations are conducted in the following manner.

First, using a connector equipped with a hollow double pointed needle, a liquid vial container prefilled with a liquid is connected to one of the two points of the double pointed needle, a drug vial container filled with a powdery drug is connected to the other, and the liquid in the liquid vial container is transferred into the drug vial container. As a result, the drug in the drug vial container is dissolved in the liquid See, for example, Japanese Patent Laid-Open No. 2009-153720. Note that the inside of the drug vial container is kept in a negative pressure state, so that the transfer of the liquid from the liquid vial container into the drug vial container is performed smoothly.

Next, the double pointed needle is pulled out from the drug vial container, a puncture needle having a sharp needle point at its distal and connected to a syringe is made to pierce through a plug body of the drug vial container, whereby the liquid medicine in the drug vial container is sucked and filled into an outer cylinder of the syringe.

Then, using the syringe thus filled with the liquid medicine, drip infusion or administration of an anti-adhesion material or a biological tissue adhesive or the like is carried out.

Meanwhile, depending on the medical institution, a syringe filled with a liquid (hereinafter referred to as "liquid-filled syringe") may be used in place of the liquid vial container. In this case, the operation is carried out through a preparation step as follows. First, one syringe in an empty state, or an unused state, and one flexible container prefilled with a liquid are prepared. The empty syringe and the flexible container are connected. Next, in this connected state, the liquid is transferred into the syringe. As a result, a liquid-filled syringe is obtained.

In the case of preparing a plurality of liquid-filled syringes, however, the preparation step must be repeated for each of the liquid-filled syringes. Therefore, until all the liquid-filled syringes are prepared, a period of time corresponding to the number of liquid-filled syringes to be prepared would be consumed. Furthermore, depending on the person who carries out the preparation step, the amount of the liquid filled in each liquid-filled syringe would vary from syringe to syringe.

SUMMARY

In a medical kit and a liquid filling method according to the present disclosure, a liquid can be filled into syringes through an easy operation, rapidly and in the proper amounts.

(1) An embodiment of a medical kit includes: one liquid storage container including a flexible container main body preliminarily storing a liquid therein, and a container-side mouth portion which communicates with the container main body and which is configured to discharge the liquid inside the container main body therethrough, at least two syringes each including a syringe outer cylinder having a syringe-side mouth portion through which a liquid can flow in and out, and a gasket slidable within the syringe outer cylinder, a connector including a container-side connection portion to which the container-side mouth portion is connected in a liquid-tight manner, and syringe-side connection portions which communicate with the container-side connection portion and to which the syringe-side mouth portions are individually connected in a liquid-tight manner; and a regulating mechanism collectively regulating limits of movement of the gaskets toward a side opposite to the container-side mouth portion, wherein the syringes are collectively filled with the liquid by conducting an operation to feed the liquid in the liquid storage container from the liquid storage container side to the syringe side in a condition in which the liquid storage container and the syringes in an unused state of being not yet filled with liquid are connected to each other through the connector, the operation being performed until the regulated limits of movement are reached.

(2) A further embodiment of a medical kit includes the medical kit as described in the above paragraph (1), wherein the liquid feeding operation is performed by pressing the container main body.

(3) Further embodiments of a medical kit include the medical kit as described in the above paragraph (1) or (2), wherein the regulating mechanism has a connection member connecting the gaskets to each other, and a majority portion of the connection member is inserted in the syringe outer cylinders in the unused state.

(4) Further embodiments of a medical kit include the medical kit as described in the above paragraph (3), wherein the regulating mechanism includes a first engaging portion provided in one of the connection member and the syringe outer cylinder, and a second engaging portion which is provided in an other of the connection member and the syringe outer cylinder and engages with the first engaging portion at the limit of movement.

(5) Further embodiments of a medical kit include the medical kit as described in the above paragraph (3) or (4), wherein the first engaging portion is composed of a cutout formed by cutting out in the connection member, and the second engaging portion is composed of a projecting piece projecting from the syringe outer cylinder.

(6) Further embodiments of a medical kit include the medical kit as described in the above paragraph (4) or (5), wherein engagement between the first engaging portion and the second engaging portion can be cancelled and the regulating mechanism has an operation section for a cancelling operation to cancel the engagement.

(7) Further embodiments of a medical kit include the medical kit as described in any one of the above paragraphs (1) to (6), wherein the regulating mechanism is configured to maintain the state of the limits of movement.

(8) Further embodiments of a medical kit include the medical kit as described in any one of the above paragraphs (1) to (7), wherein the syringe outer cylinders differ from one another in size.

(9) Further embodiments of a medical kit include the medical kit as described in any one of the above paragraphs (1) to (8), wherein the syringes constitute a syringe assembly in which they are connected to one another.

(10) Further embodiments of a medical kit include the medical kit as described in any one of the above paragraphs (1) to (9), wherein the container-side connection portion and each of the syringe-side connection portions are tubular portions protruding in opposite directions.

(11) Further embodiments of a medical kit include the medical kit as described in any one of the above paragraphs (1) to (10), wherein the liquid is a dissolving liquid or a diluting liquid.

(12) In an embodiment of a method of filling a liquid into syringes in an unused state of being not yet filled with liquid, the method is performed by use of one liquid storage container including a flexible container main body preliminarily storing a liquid therein, and a container-side mouth portion which communicates with the container main body and which is configured to discharge the liquid inside the container main body therethrough, at least two syringes each including a syringe outer cylinder having a syringe-side mouth portion through which a liquid can flow in and out, and a gasket slidable within the syringe outer cylinder, a connector including a container-side connection portion to which the container-side mouth portion is connected in a liquid-tight manner, and syringe-side connection portions which communicate with the container-side connection portion and to which the syringe-side mouth portions are individually connected in a liquid-tight manner and a regulating mechanism collectively regulating limits of movement of the gaskets toward a side opposite to the container-side mouth portion. The method comprises filling the liquid into the syringes collectively by conducting an operation to feed the liquid in the liquid storage container from the liquid storage container side to the syringe side in a condition in which the liquid storage container and the syringes in the unused state are connected to each other through the connector, the operation being performed until the regulated limits of movement are.

A liquid feeding operation of feeding a liquid in a liquid storage container from the liquid storage container side to the side of syringes in an unused state of being not yet filled with liquid, in a condition in which the liquid storage container and the unused syringes are connected to each other through a connector, can be carried out easily. By performing this liquid feeding operation, the liquid can be rapidly filled into the syringes in the proper amounts.

DETAILED DESCRIPTION

A medical kit and a liquid filling method according to the present disclosure will be described in detail below on the basis of a preferred embodiment illustrated in the accompanying drawings. Note that in the following description, for convenience of explanation, the upper side in FIGS. 4 to 6 will be referred to as "proximal" or "upper (side)," and the lower side as "distal" or "lower (side)." In addition, the upper side in FIGS. 2, 3, and 7 will be referred to as "distal" or "upper (side)," and the lower side as "proximal" or "lower (side)."

As illustrated in FIGS. 1 to 6, a medical kit 100 includes a first syringe assembly (syringe assembly) 10, a second syringe assembly 20, a first connector (connector) 3, a second connector 4, a liquid storage container 5, a first drug storage container 6*a*, and a second drug storage container 6*b*, single ones of these medical devices being collectively packaged, for example, in the same package (not shown).

Figure 2:
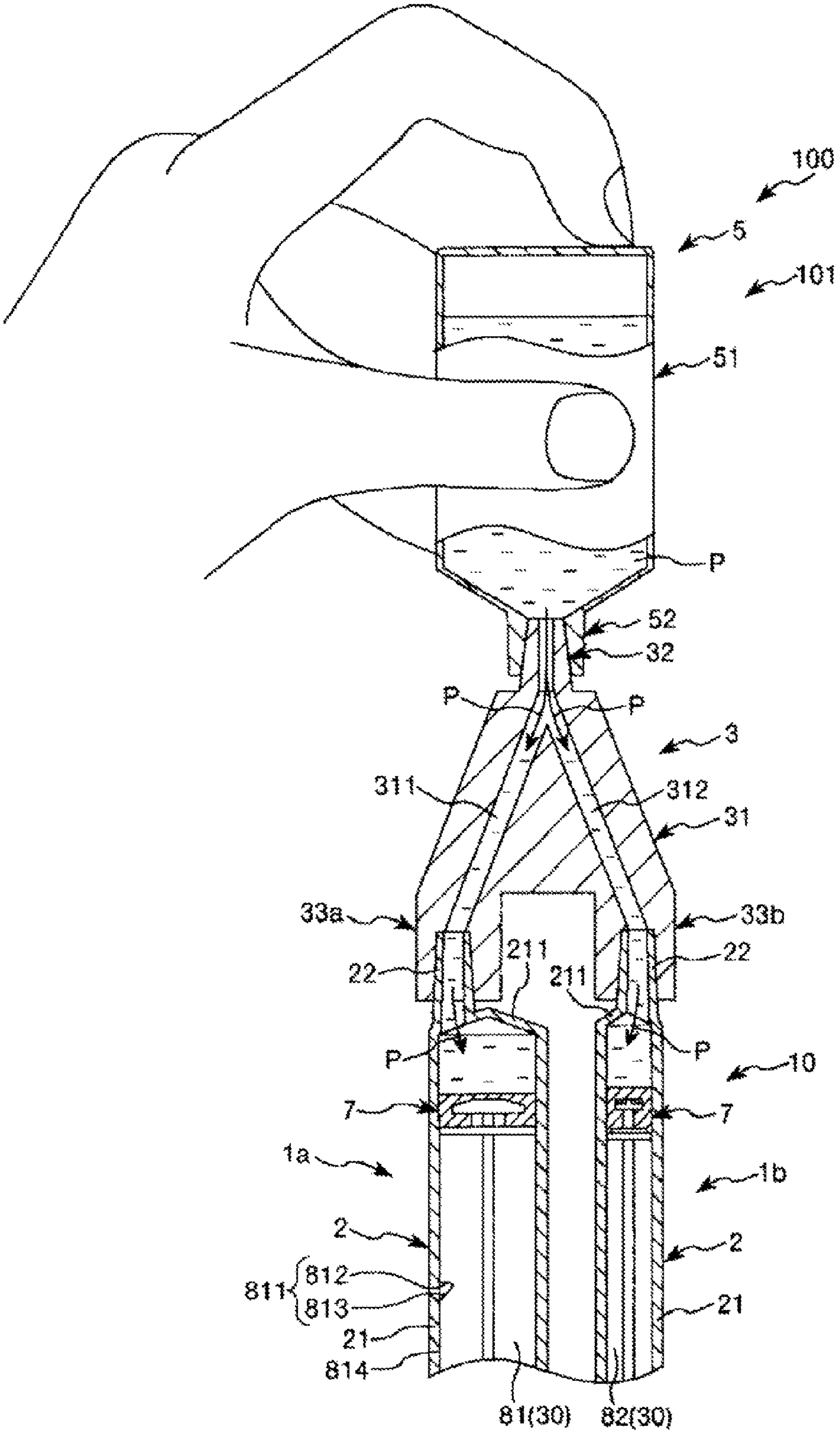
FIG. 2 is a longitudinal sectional view for sequentially depicting the method of using the medical kit.
Figure 3:
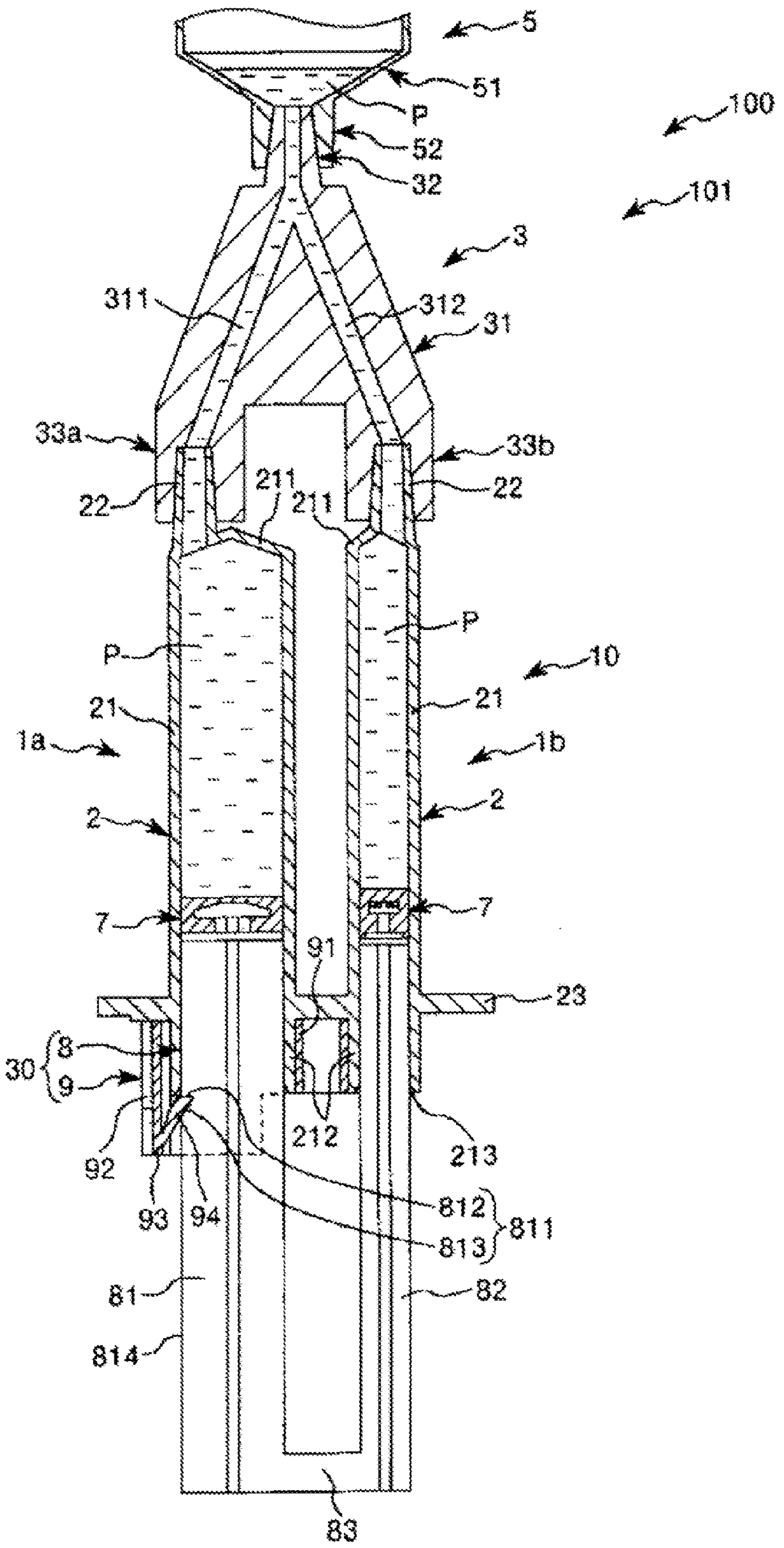
FIG. 3 is a longitudinal sectional view for sequentially depicting the method of using the medical kit.

In a process of using this medical kit 100, a first assembly 101 in which the first syringe assembly 10, the first connector 3, and the liquid storage container 5 are assembled together is obtained (see FIGS. 2 and 3). Thereafter, the first syringe assembly 10 is detached from the first assembly 101, and a second assembly 102 in which the first syringe assembly 10, the second connector 4, the first drug storage container 6*a*, and the second drug storage container 6*b* are assembled together is obtained (see FIGS. 4 and 5). Further, the first drug storage container 6*a* and the second drug storage container 6*b* are detached from the second assembly 102, and a third assembly 103 in which the first drug storage container 6*a* and the second drug storage container 6*b* and the second syringe assembly 20 are assembled together is obtained (see FIG. 6).

As depicted in FIGS. 1 to 5, the first syringe assembly 10 is a device which is once filled with a liquid P from the liquid storage container 5 and which supplies the liquid P filled therein into the first drug storage container 6*a* and the second drug storage container 6*b*.

The first syringe assembly 10 has a syringe 1*a* and a syringe 1*b* connected in parallel to each other. The syringe 1*a* and the syringe 1*b* are substantially the same in configuration except for a difference in diametric size, or maximum internal volume. In view of this, therefore, the syringe 1*a* will be described below on a representative basis.

The syringe 1*a* includes a syringe outer cylinder 2 and a gasket 7. The syringe outer cylinder 2 includes a barrel portion 21 in the form of a bottomed cylinder, and a mouth portion (syringe-side mouth portion) 22 protruding from a bottom portion which constitutes a distal wall portion 211 of the barrel portion 21.

The barrel portion 21 has an inside diameter and an outside diameter which are individually constant along a center axis direction of the barrel portion 21. Note that the inside diameter of the barrel portion 21 of the syringe 1*a* is greater than the inside diameter of the barrel portion 21 of the syringe 1*b*. Similarly, the outside diameter of the barrel portion 21 of the syringe 1*a* is greater than the outside diameter of the barrel portion 21 of the syringe 1*b*.

In addition, the barrel portion 21 of the syringe 1*a* and the barrel portion 21 of the syringe 1*b* are connected to each other at their intermediate portions in their center axis directions through a flange portion 23 having a plate-like shape. By this connection, the positional relationship between the syringe 1*a* and the syringe 1*b* is regulated, in other words, a state in which the syringe 1*a* and the syringe 1*b* are connected in parallel to each other is maintained. Note that in the syringe 1*a*, the barrel portion 21 has a protruding portion 212 which protrudes proximally from the flange portion 23 and to which a lock member 9 of a regulating mechanism 30 described later can be mounted.

The mouth portion 22 is a portion which is in the shape of a tube smaller than the barrel portion 21 in diametric size and which communicates with the barrel portion 21. Through the mouth portion 22, a liquid P can flow into the barrel portion 21 and, reversely, the liquid P can flow out of the barrel portion 21. Note that the mouth portion 22 is disposed at a position eccentric with respect to the center of the distal wall portion 211 of the barrel portion 21. In addition, an outer peripheral portion of the mouth portion 22 has a tapered shape where its outside diameter gradually decreases along the distal direction. In the present embodiment, the outside diameter of the mouth portion 22 of the syringe 1*a* and the outside diameter of the mouth portion 22 of the syringe 1*b* are equal.

The material constituting the syringe outer cylinder 2 is not specifically restricted. For example, resin materials such as polypropylene, cyclic polyolefin, polyester, and poly(4-methylpentene-1) are preferably used in view of easy moldability thereof. Note that the constituent material of the syringe outer cylinder 2 is preferably substantially transparent for assuring visibility of the inside.

Figure 4:
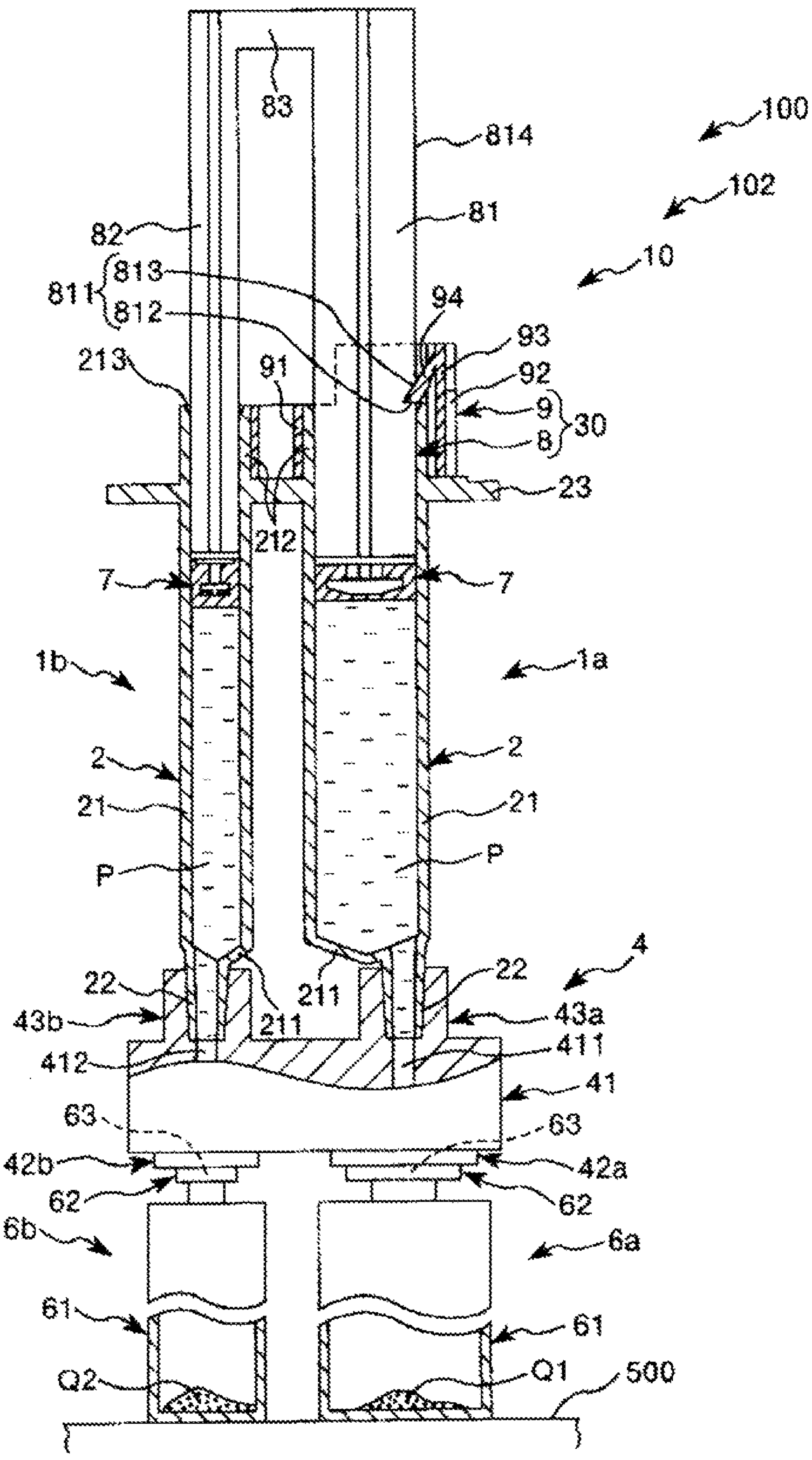
FIG. 4 is a longitudinal sectional view for sequentially depicting the method of using the medical kit.
Figure 5:
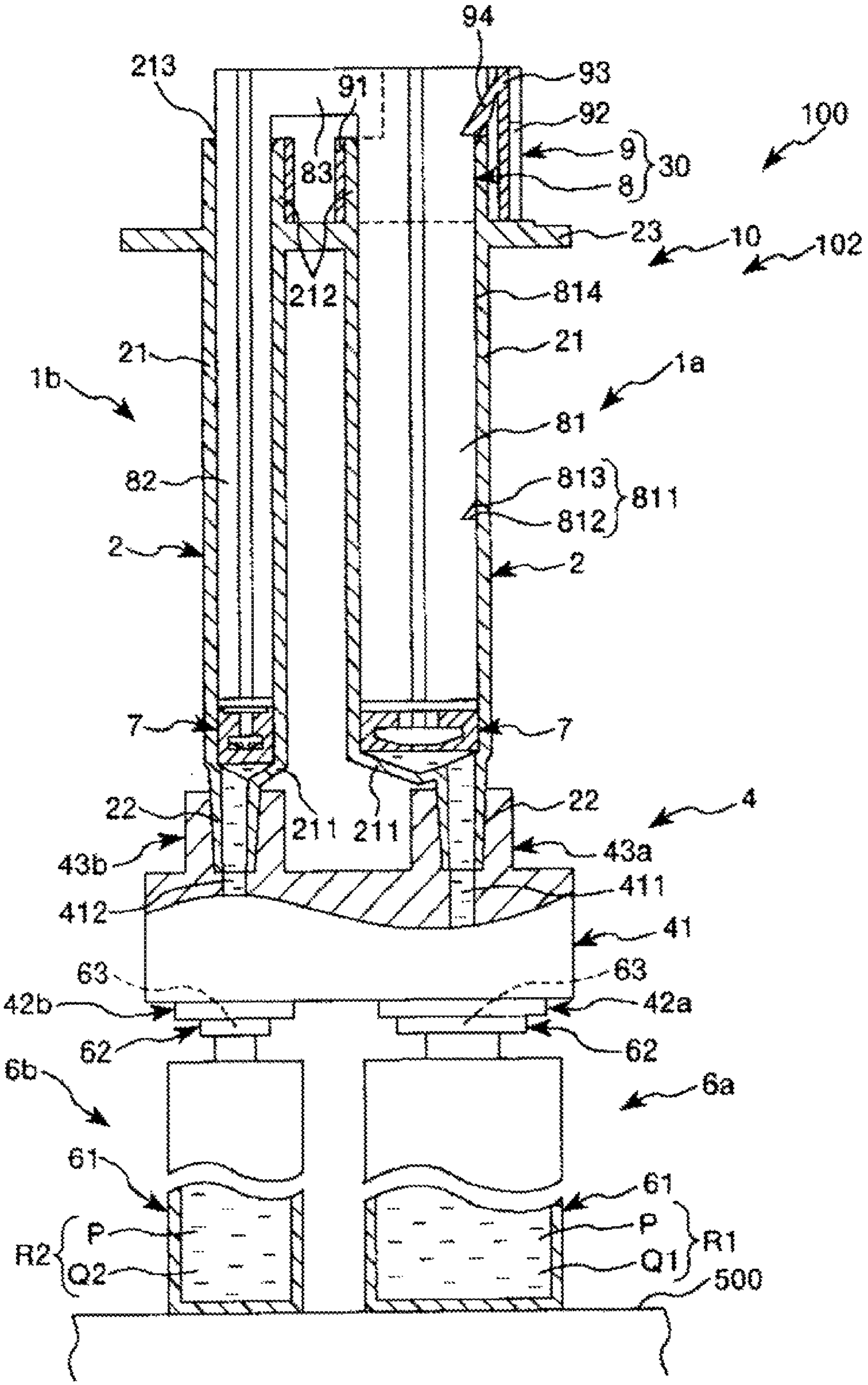
FIG. 5 is a longitudinal sectional view for sequentially depicting the method of using the medical kit.

The gasket 7 is configured from an elastic body having a cylindrical or disk-like shape. The gasket 7 is accommodated in the barrel portion 21 (syringe outer cylinder 2) and is slidable within the barrel portion 21. As shown in FIG. 4, a liquid P can be filled in a space surrounded by the gasket 7 and the barrel portion 21. By moving the gasket 7 distally, starting from this filled state, the liquid P can be discharged through the mouth portion 22, as depicted in FIG. 5.

The material constituting the gasket 7 is not specifically restricted. Examples of the material usable include elastic materials such as various rubber materials (e.g., silicone rubber, etc.), various thermoplastic elastomers based on polyurethane or the like, and mixtures of them.

Figure 6:
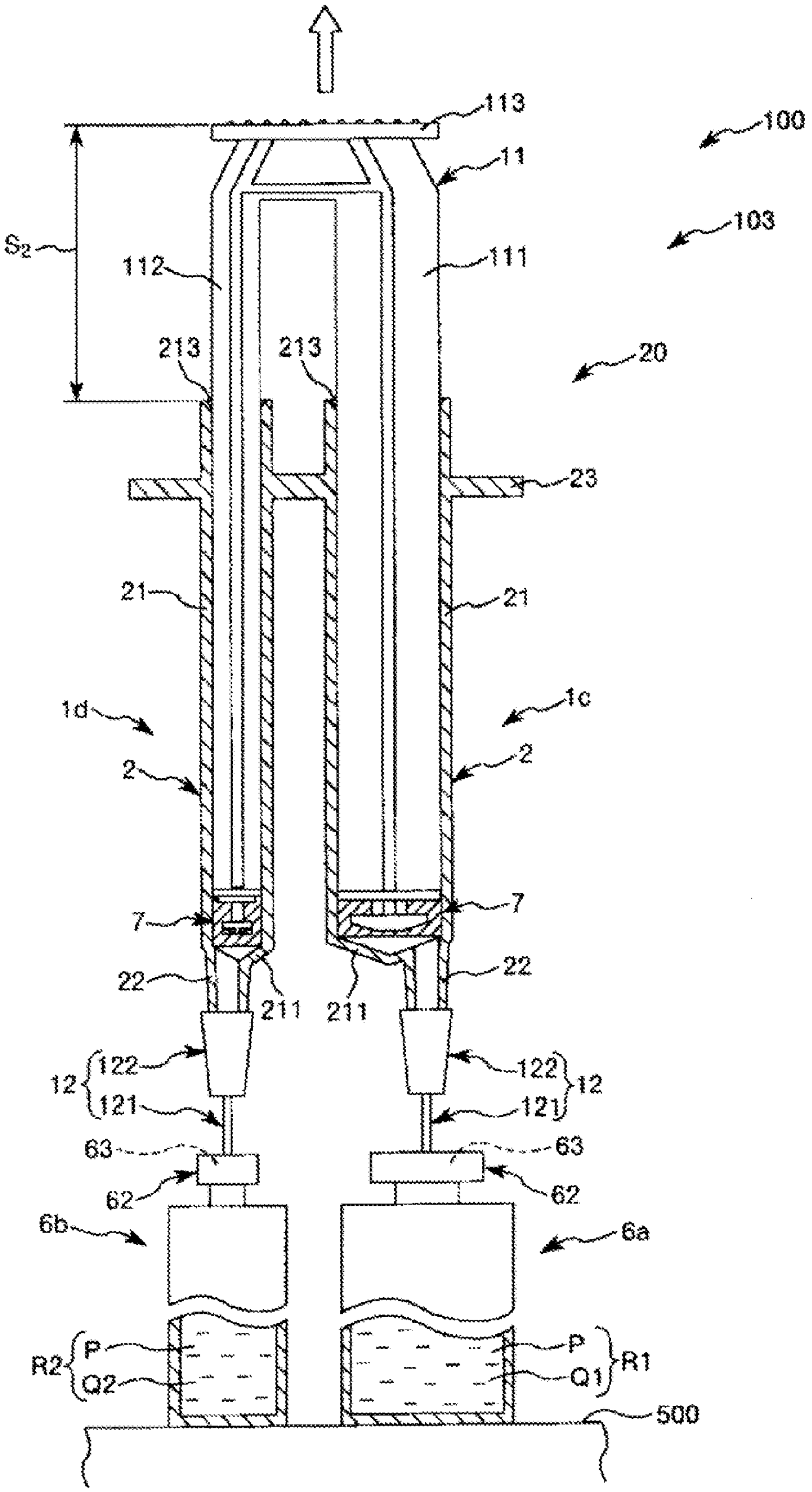
FIG. 6 is a longitudinal sectional view for sequentially depicting the method of using the medical kit.
Figure 7:
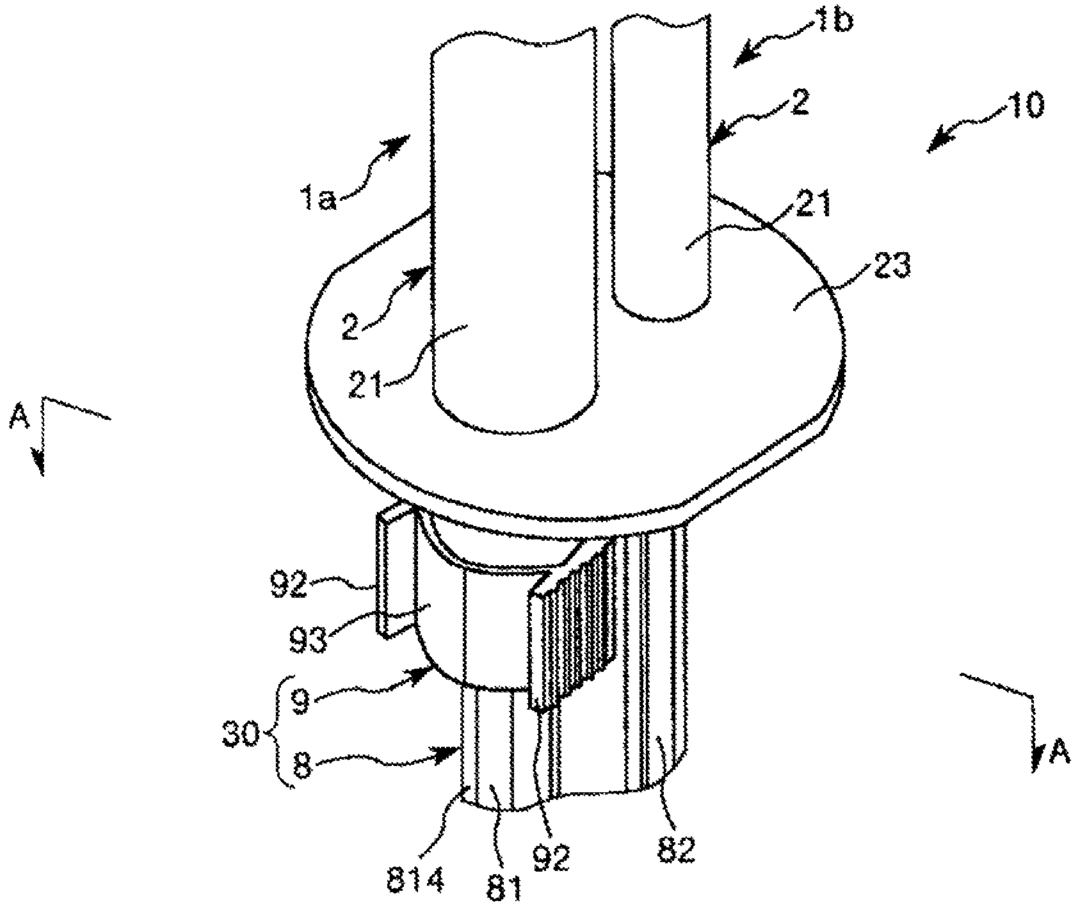
FIG. 7 is a perspective view showing the state depicted in FIG. 3.

As shown in FIG. 6, the second syringe assembly 20 is to be filled with a liquid medicine R1 prepared in the first drug storage container 6*a* and a liquid medicine R2 prepared in the second drug storage container 6*b*.

The second syringe assembly 20 includes a syringe 1*c* and a syringe 1*d* connected in parallel to each other. The syringe 1*c* and the syringe 1*d* are substantially the same in configuration except for a difference in size. In the present embodiment, the syringe 1*c* is configured in the same manner as the syringe 1*a*, and the syringe 1*d* is configured in the same manner as the syringe 1*b*.

In addition, the second syringe assembly 20 further includes a plunger 11 and two puncture needles 12.

The plunger 11 is a member for collectively operating the gaskets 7. The plunger 11 includes a plunger portion 111 connected to the gasket 7 of the syringe 1*c*, a plunger portion 112 connected to the gasket 7 of the syringe 1*d*, and a flange portion 113 as an operation section.

The plunger portion 111 is elongate in shape, and its distal portion is connected to the gasket 7 of the syringe 1*c*. Similarly, the plunger portion 112 is elongate in shape, and its distal portion is connected to the gasket 7 of the syringe 1*d*. The method for the connection here is not specifically restricted; for example, the connection may be performed by a screwing method or a fitting method or the like. Note that the plunger portion 111 is greater than the plunger portion 112 in diametric size.

The flange portion 113 is plate-like in shape, and, from its distal face, the plunger portions 111 and 112 individually extend distally.

The two puncture needles 12 are each composed of a hollow needle 121 having a sharp needle point at the distal thereof, and a hub 122 supporting a proximal portion of the hollow needle 121.

The hub 122 of one puncture needle 12 of the two puncture needles 12 is attached to the mouth portion 22 of the syringe 1*c*, whereby the inside of the syringe 1*c* and the hollow needle 121 are made to communicate with each other through the hub 122. As a result, in the state as depicted in FIG. 6, the liquid medicine R1 prepared in the first drug storage container 6*a* can be filled into the syringe 1*c*.

In addition, the hub 122 of the other puncture needle 12 is attached to the mouth portion 22 of the syringe 1*d*, whereby the inside of the syringe 1*d* and the hollow needle 121 are made to communicate with each other through the hub 122. As a result, in the state as depicted in FIG. 6, the liquid medicine R2 prepared in the second drug storage container 6*b* can be filled into the syringe 1*d*.

Figure 1:
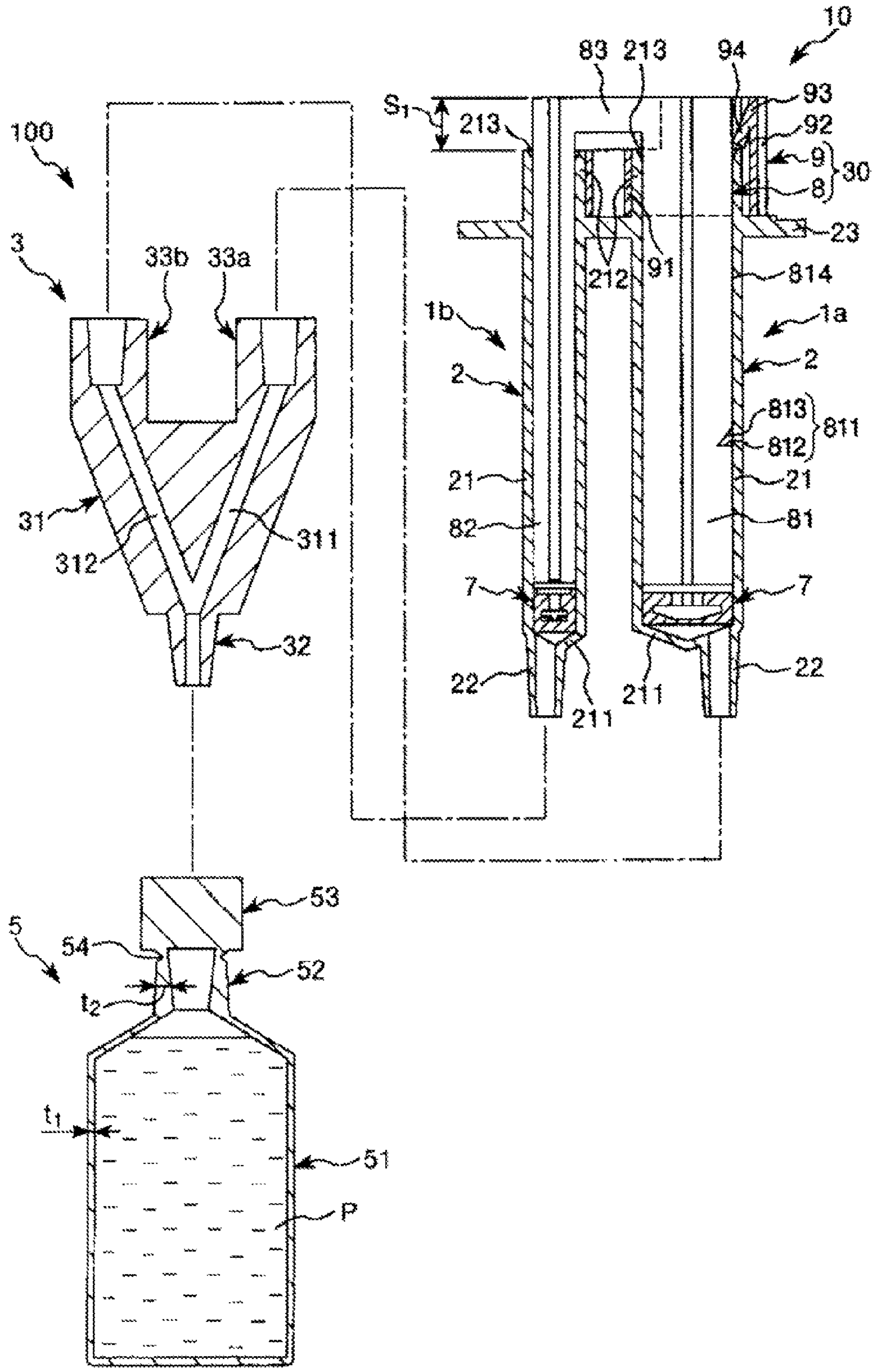
FIG. 1 is a longitudinal sectional view for sequentially depicting a method of using a medical kit.

As shown in FIG. 1, the liquid storage container 5 is for storing the liquid P. The liquid storage container 5 includes a flexible container main body 51, a mouth portion (container-side mouth portion) 52 provided at an upper portion of the container main body 51, a seal portion 53 for sealing the mouth portion 52 in a liquid-tight manner, and an easily breakable portion 54 provided between the mouth portion 52 and the seal portion 53, with these portions being formed integrally.

The container main body 51 is in the shape of a bottomed cylinder, and is preliminarily filled therein with the liquid P. The amount of the liquid P filled is so set that the liquid P can be sufficiently distributed into the syringes 1*a* and 1*b* of the first syringe assembly 10. Note that in the present embodiment, the liquid P is water for injection.

The mouth portion 52 is a portion in the shape of a tube smaller than the container main body 51 in diametric size, and communicates with the container main body 51. An inner peripheral portion of the mouth portion 52 has a tapered shape where its inside diameter gradually decreases along a downward direction. The average thickness $t_1$ of a wall portion of the container main body 51 is smaller than the average thickness $t_2$ of a wall portion of the mouth portion 52. This assures that the container main body 51 is greater in flexibility than the mouth portion 52. Therefore, when discharging the liquid P in the container main body 51 through the mouth portion 52, as shown in FIG. 2, the discharging operation can be carried out easily and reliably by pressing the container main body 51.

The seal portion 53 is a portion in the form of a small piece. The easily breakable portion 54 is a portion composed of a thin-walled portion. In order to remove the seal portion 53 and open the mouth portion 52, first, the container main body 51 is grasped by one hand, and the seal portion 53 is grasped by the other hand. Next, keeping this state, the seal portion 53 is rotated relative to the container main body 51. As a result, the easily breakable portion 54 is twisted, and is broken when an endurance limit (at which breakage occurs) is reached. By this breakage (rupture), the seal portion 53 is removed, and the mouth portion 52 is opened.

The material constituting the liquid storage container 5 is not specifically restricted, and, for example, various flexible resin materials such as polyethylene, polypropylene, and polyethylene terephthalate (PET) can be used.

As shown in FIG. 4, the first drug storage container 6*a* is for containing a drug Q1, and the second drug storage container 6*b* is for storing a drug Q2. The first drug storage container 6*a* and the second drug storage container 6*b* are substantially the same in configuration except for differences in size, or internal volume, and in the drug stored. In view of this, therefore, the first drug storage container 6*a* will be described below on a representative basis.

The first drug storage container 6*a* includes a rigid container main body 61, a mouth portion 62 provided at an upper portion of the container main body 61, and a plug body 63 for sealing the mouth portion 62 in a liquid-tight manner.

The container main body 61 is in the shape of a bottomed cylinder, and is preliminarily filled therein with the drug Q1, which is powdery for example. When the drug Q1 is dissolved in the liquid P, the liquid medicine R1 is obtained (see FIG. 5).

The mouth portion 62 is a portion in the form of a cylinder smaller than the contained main body 61 in diametric size, and communicates with the container main body 61. Note that the mouth portion 62 is preferably formed to be integral with the container main body 61. In this case, the materials constituting the container main body 61 and the mouth portion 62 are not particularly limited, and, for example, various glass materials can be used.

The plug body 63 is composed of an elastic body having a cylindrical or disk-like shape, and is attached to the mouth portion 62 by fitting. The plug body 63 is to be punctured by the hollow needle 121 of the puncture needle 12 (see FIG. 6). Note that the material constituting the plug body 63 is not specifically restricted; for example, the same material as the constituent material of the gasket 7 can be used.

On the other hand, in the second drug storage container 6*b*, the drug Q2, which is powdery for example, is preliminarily stored in the container main body 61. When the drug Q2 is dissolved in the liquid P, the liquid medicine R2 is obtained (see FIG. 5).

In the case of mixing the liquid medicine R1 and the liquid medicine R2 in a predetermined mixing ratio and making the resulting mixed solution a biological tissue adhesive, one of the liquid medicine R1 and the liquid medicine R2 may be thrombin, and the other drug may be fibrinogen. In the case of making the mixed solution an anti-adhesion material, one of the drugs in the liquid medicines may be carboxymethyl dextrin modified with a succinimidyl group, and the other may be a mixture of sodium hydrogen carbonate and sodium carbonate.

As shown in FIGS. 1 to 3, the first connector 3 includes a main body portion 31, a connection portion (container-side connection portion) 32 provided at the distal side of the main body portion 31, and connection portions (syringe-side connection portions) 33*a* and 33*b* provided at the proximal side of the main body portion 31, with these portions being formed integrally.

The main body portion 31 is a portion which is flat shaped externally. The main body portion 31 is formed therein with channels 311 and 312.

The connection portion 32 is a tubular portion formed to protrude distally. A peripheral portion of the connection portion 32 has a tapered shape where its outside diameter gradually decreases along the distal direction. As shown in FIGS. 2 and 3, when the mouth portion 52 of the liquid storage container 5 which has been unsealed (opened) is inserted into the inside of the connection portion 32, the mouth portion 52 can be connected to the connection portion 32 in a liquid-tight manner.

The connection portion 33*a* and the connection portion 33*b* are portions which are disposed adjacent to each other, with the center axis of the main body portion 31 therebetween, and which each have a tubular shape formed to protrude proximally. The connection portion 33*a* communicates with the connection portion 32 through the channel 311, and the connection portion 33*b* communicates with the connection portion 32 through the channel 312. In addition, inner peripheral portions of the connection portions 33*a* and 33*b* each have a tapered shape where the inside diameter gradually decreases along the distal direction. As shown in FIGS. 2 and 3, when the mouth portion 22 of the syringe 1*a* of the first syringe assembly 10 is inserted into the inside of the connection portion 33*a*, the mouth portion 22 can be connected to the connection portion 33*a* in a liquid-tight manner. Similarly, when the mouth portion 22 of the syringe 1*b* of the first syringe assembly 10 is inserted into the inside of the connection portion 33*b*, the mouth portion 22 can be connected to the connection portion 33*b* in a liquid-tight manner.

In the first connector 3, the connection portion 32 and the connection portions 33*a* and 33*b* protrude in opposite directions. This ensures that in the first assembly 101, one side of the first connector 3 can be made to be a side for supplying the liquid P is supplied and the other side of the first connector 3 can be made to be a side for being supplied with the liquid P. Then, when the side for supplying the liquid P is situated on the upper side, as shown in FIGS. 2 and 3, an operation of supplying the liquid P can be carried out easily.

As shown in FIGS. 4 and 5, the second connector 4 includes a main body portion 41, connection portions 42*a* and 42*b* which are provided at the distal side of the main body portion 41, and connection portions 43*a* and 43*b* which are provided at the proximal side of the main body portion 41.

The main body portion 41 is a portion which is block-like in external shape. The main body portion 41 is formed therein with channels 411 and 412.

The connection portion 42*a* and the connection portion 42*b* are disposed adjacent to each other, with the center axis of the main body portion 41 therebetween. Inside the connection portion 42*a* is incorporated a metallic hollow needle (not shown) which communicates with the channel 411. By connecting the mouth portion 62 of the first drug storage container 6*a* to the connection portion 42*a*, as shown in FIGS. 4 and 5, the plug body 63 sealing the mouth portion 62 can be pierced through. Similarly, inside the connection portion 42*b* is incorporated a metallic hollow needle (not shown) which communicates the channel 412. By connecting the mouth portion 62 of the second drug storage container 6*b* to the connection portion 42*b*, the plug body 63 sealing the mouth portion 62 can be pierced through.

The connection portion 43*a* and the connection portion 43*b* are tubular portions which are disposed adjacent to each other, with the center axis of the main body portion 31 therebetween, and which are formed to protrude proximally. The connection portion 43*a* communicates with the hollow needle of the connection portion 42*b* through the channel 411, and the connection portion 43*b* communicates with the hollow needle of the connection portion 42*b* through the channel 412. Inner peripheral portions of the connection portions 43*a* and 43*b* have tapered shapes where their inside diameters gradually decreases along the distal direction.

Then, when the mouth portion 22 of the syringe 1*a* of the first syringe assembly 10 is inserted into the inside of the connection portion 43*a*, as shown in FIGS. 4 and 5, the mouth portion 22 can be connected to the connection portion 43*a* in a liquid-tight manner. Similarly, when the mouth portion 22 of the syringe 1*b* of the first syringe assembly 10 is inserted into the inside of the connection portion 43*b*, the mouth portion 22 can be connected to the connection portion 43*b* in a liquid-tight manner.

The material or materials constituting the first connector 3 and the second connector 4 (exclusive of the hollow needles) are not particularly limited; for example, the same material as the constituent material of the syringe outer cylinder 2 can be used.

Meanwhile, as shown in FIGS. 1 and 3 to 5, the first syringe assembly 10 is provided with a regulating mechanism 30. The regulating mechanism 30 is a mechanism for collectively regulating limits of movement of the gaskets 7 of the syringes 1*a* and 1*b* toward a side opposite to the mouth portions 22, namely, toward the proximal side. The regulating mechanism 30 is composed of a connection member 8 which connects the gaskets 7 of the syringes 1*a* and 1*b* to each other, and the lock member 9 which is mounted to the protruding portion 212 of the syringe 1*a*.

As shown in FIG. 1, the connection member 8 includes an elongate plunger portion 81, an elongate plunger portion 82 parallel to and spaced from the plunger portion 81, and a plate-shaped portion 83 arranged between the plunger portion 81 and the plunger portion 82.

The plunger portion 81 is composed mainly of a plate piece having a cross-like cross-sectional shape, and a distal portion thereof is connected to the gasket 7 of the syringe 1*a*. Similarly, the plunger portion 82 is composed mainly of a plate piece having a cross-like cross-sectional shape, and a distal portion thereof is connected to the gasket 7 of the syringe 1*b*. The method for the connection here is not particularly limited, and, for example, a screwing method, a fitting method and the like can be used. Note that the plunger portion 81 is greater than the plunger portion 82 in diametric size.

The plate-shaped portion 83 connects a proximal portion of the plunger portion 81 and a proximal portion of the plunger portion 82 to each other. The thickness of the plate-shaped portion 83 is equal to the thickness of the plate piece constituting the plunger portion 81 and the plunger portion 82.

In addition, the plunger portion 81 is provided with a first engaging portion 811 at an intermediate portion in the longitudinal direction thereof. As shown in FIGS. 3 and 4, the first engaging portion 811 can engage a second engaging portion 94 provided on the lock member 9 (the syringe 1*a* side). The first engaging portion 811 is composed of a cutout formed by cutting out part of the plunger portion 81 in a wedge shape. The first engaging portion 811 is formed with a locking surface 812 orthogonal to the longitudinal direction of the plunger portion 81, and an inclined surface 813 inclined against the longitudinal direction of the plunger portion 81.

Figure 8A:
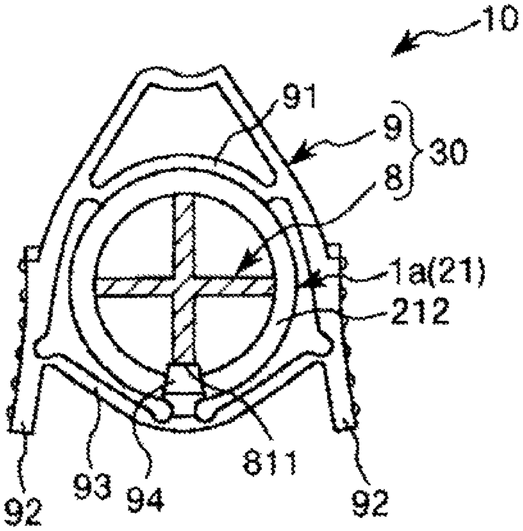
FIG. 8(*a*) shows a sectional view taken along line A-A of FIG. 7 of a first part of a cancelling operation, and FIG. 8(*b*) shows a sectional view taken along line A-A of FIG. 7 of a second part of a cancelling operation.
Figure 8B:
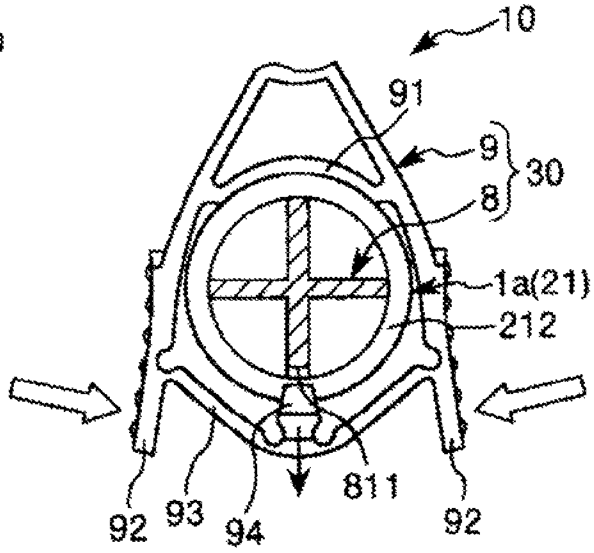

As shown in FIGS. 8(*a*) and 8(*b*), the lock member 9 includes a mounting portion 91 to be mounted to the protruding portion 212 of the syringe 1*a*, a pair of operation pieces 92 disposed on both sides of the mounting portion 91, an arched portion 93 disposed between the operation pieces 92, and the second engaging portion 94 provided inside of the arched portion 93.

The mounting portion 91 is disposed between the protruding portion 212 of the syringe 1*a* and the protruding portion 212 of the syringe 1*b*. In this disposition condition, the mounting portion 91 receives a reaction force from the syringe 1*b* side, to be thereby pressed against the syringe 1*a* side. As a result, the mounting portion 91 is mounted onto the protruding portion 212 of the syringe 1*a*.

The pair of operation pieces 92 are operation sections to be operated when it is desired to cancel the engagement between the first engaging portion 811 and the second engaging portion 94. This cancelling operation (disengaging operation) is conducted by moving the operation pieces 92 closer to each other as depicted in FIG. 8(*b*), starting from the state shown in FIG. 8(*a*). By this, the arched portion 93 is bent to the outer side, and the second engaging portion 94 is spaced apart from the first engaging portion 811 by an amount corresponding to the bending, whereby the engagement between the first engaging portion 811 and the second engaging portion 94 is cancelled.

As shown in FIGS. 3 and 4, the second engaging portion 94 engages with the first engaging portion 811 of the connection member 8 at the limits of movement of the gaskets 7 of the syringes 1*a* and 1*b* toward the proximal side. By this engagement, desired amounts of the liquid P are filled individually into the syringes 1*a* and 1*b* in an assured manner.

The second engaging portion 94 is composed of a projecting piece which projects to the inner side of the arched portion 93 and which is inclined against the plunger portion 81 of the connection member 8. When the second engaging portion 94 thus configured engages the first engaging portion 811 of the connection member 8, a state in which the gaskets 7 of the syringes 1*a* and 1*b* are located at their limits of movement can be thereby maintained. As a result, it is possible to prevent the gaskets 7 of the syringes 1*a* and 1*b* from inadvertently moving distally to take in the liquid P excessively, and to prevent the gaskets 7 from inadvertently moving proximally to discharge the liquid P needlessly.

Note that as shown in FIGS. 1 and 5, in a state in which the second engaging portion 94 is not in engagement with the first engaging portion 811, the second engaging portion 94 is elastically deformed by being pressed to the outer side by that part of the plunger portion 81 which is located on the proximal side with reference to the first engaging portion 811 (this part will hereinafter be referred to as "pressing regulating part 814").

The materials constituting the connection member 8 and the lock member 9 are not specifically restricted; for example, the same material as the constituent material of the syringe outer cylinder 2 can be used.

Now, a method of using the medical kit 100 will be described below referring to FIGS. 1 to 6.

[1] First, as depicted in FIG. 1, the first syringe assembly 10, the first connector 3, and the liquid storage container 5 are prepared by picking them up from the medical kit 100 in an unused state. Note that the first syringe assembly 10 is preliminarily provided with the regulating mechanism 30.

In this instance, in the first syringe assembly 10, the syringes 1*a* and 1*b* have not yet been filled with the liquid P, and the gaskets 7 are individually located on the deepest side in the syringe outer cylinders 2, namely, are in the state of having reached the distal wall portions 211 of the syringe outer cylinders 2.

In the regulating mechanism 30, the second engaging portion 94 of the lock member 9 has not yet engaged the first engaging portion 811 of the connection member 8, and is in the state of being elastically deformed by being pressed to the outer side by the pressing regulating part 814.

In addition, the liquid storage container 5 is in an unsealed (unopened) state. Now, therefore, the liquid storage container 5 is unsealed (opened) as aforementioned.

[2] Next, as shown in FIG. 2, the first syringe assembly 10 and the liquid storage container 5 are connected to each other through the first connector 3, to assemble the first assembly 101. Then, the first assembly 101 is inverted upside down with respect to the state depicted in FIG. 1. As a result, the liquid storage container 5 is located on the upper side, whereas the first syringe assembly 10 is located on the lower side. Note that, for example, a left hand is put on the liquid storage container 5, and a right hand is put on the first syringe assembly 10.

Thereafter, a liquid feeding operation of feeding the liquid P in the liquid storage container 5 from the liquid storage container 5 side to the first syringe assembly 10 side is performed. This liquid feeding operation is conducted by crushing the container main body 51 of the liquid storage container 5 by pressing with the left hand. Owing to an interaction of this pressing force and the gravity, the liquid P is permitted to flow down rapidly and easily.

Note that as depicted in FIG. 1, the connection member 8 in the state before the liquid feeding operation has a majority portion thereof inserted in the syringe outer cylinders 2, and parts of the connection member 8 protruding slightly from proximal opening portions 213 of the syringe outer cylinders 2. The protrusion amount in this instance is represented as "$s_1$."

On the other hand, as shown in FIG. 6, in the second syringe assembly 20 in an unused state, also, the gaskets 7 are individually located on the deepest side in the syringe outer cylinders 2. The plunger 11 in this state has its parts protruding from the proximal opening portions 213 of the syringe outer cylinders 2. The protrusion amount in this instance is represented as "$s_2$."

Comparing the protrusion amount $s_1$ and the protrusion amount $s_2$ with each other, the protrusion amount $s_1$ is smaller than the protrusion amount $s_2$ sufficiently. It can be said, therefore, that in the first syringe assembly 10 it is difficult to pull the connection member 8, and, in the second syringe assembly 20, it is easy to pull the plunger 11. Since it is preferable to carry out the liquid feeding operation not by pulling the connection member 8 but by pressing the liquid storage container 5, such a magnitude relationship between the protrusion amounts is effective. In addition, such a magnitude relationship can help make it easy to distinguish the first syringe assembly 101 and the second syringe assembly 20 from each other. Accordingly, at the time of assembling the first assembly 10, mistaken use the second syringe assembly 20 instead of the first syringe assembly 10 can be minimized.

Furthermore, as the number of the syringes possessed by the first syringe assembly 10 increases, it becomes accordingly easier to carry out the liquid feeding operation by pressing the liquid storage container 5 than to carry out the liquid feeding operation by pulling the connection member 8.

[3] As shown in FIG. 3, the liquid feeding operation is conducted until the first engaging portion 811 of the connection member 8 of the regulating mechanism 30 and the second engaging portion 94 of the lock member 9 engage each other and the limits of movement of the gaskets 7 are thereby regulated.

Thus, by performing an easy operation (the operations [2] and [3]) of inverting the first assembly 101 upside down and pressing the liquid storage container 5 until the gaskets 7 reach their limits of movement, it is possible to collectively fill the syringes 1*a* and 1*b* with the liquid P in the proper amounts.

In addition, the inversion of the first assembly 101 upside down can prevents air from mixing into the syringes 1*a* and 1*b* after the filling with the liquid (see FIG. 3).

[4] Subsequently, the first syringe assembly 10 is detached from the first assembly 101, and an assembly in which the second connector 4 is connected is obtained. Then, this assembly is connected to the first drug storage container 6*a* and the second drug storage container 6*b* which are put, for example, on a table 500, as shown in FIG. 4, to assemble the second assembly 102. Each of the first drug storage container 6*a* and the second drug storage container 6*b* has its inside at a negative pressure. This results in that as shown in FIG. 5, in the second assembly 102, the gaskets 7 of the first syringe assembly 10 arrive at the distal wall portions 211 of the syringe outer cylinders 2, whereby the liquid P is moved into the inside of the first drug storage container 6*a* and the second drug storage container 6*b*. Consequently, the first drug storage container 6*a* and the second drug storage container 6*b* are filled with the liquid P neither too much nor too little.

Furthermore, a method may also be adopted wherein the second connector 4 is first connected to the first drug storage container 6*a* and the second drug storage container 6*b*, thereafter the first syringe assembly 10 is connected to assemble the second assembly 102, then the second assembly 102 is put, for example, on the table 500, with the first drug storage container 6*a* and the second drug storage container 6*b* on the lower side, and a part near the plate-shaped portion 83 of the connection member 8 is pushed downward by hand.

After the liquid P is supplied, the second assembly 102 as a whole is preferably shaken. By the shaking, the drug Q1 in the first drug storage container 6*a* is reliably dissolved in the liquid P, whereby the liquid medicine R1 is prepared. Similarly, the drug Q2 in the second drug storage container 6*b* is assuredly dissolved in the liquid P, whereby the liquid medicine R2 is prepared.

[5] Next, as shown in FIG. 6, the first drug storage container 6*a* and the second drug storage container 6*b* are detached from the second assembly 102, and the second syringe assembly 20 is connected to the first drug storage container 6*a* and the second drug storage container 6*b*. By this, the third assembly 103 is assembled.

Then, the third assembly 103 is put on the table 500, with the first drug storage container 6*a* and the second drug storage container 6*b* on the lower side.

Thereafter, the plunger 11 of the second syringe assembly 20 is pulled upward. By this, the syringe 1*c* is filled with the liquid medicine R1, and the syringe 1*d* is filled with the liquid medicine R2.

The second syringe assembly 20 in which the liquid medicines R1 and R2 have been filled can be used for jetting the liquid medicines R1 and R2, while mixing them, thereby to apply the resulting mixture to, for example, a living body. At the time of this application, in the second syringe assembly 20, the flange portion 23 functions as a part on which to put a finger. While the medical kit and the liquid filling method of the present invention have been described with reference to the embodiment illustrated in the drawings, the invention is not limited to the above description. Each component constituting the medical kit and the liquid filling method can be replaced by one having an arbitrary configuration that can exhibit the same or similar function to the original. Besides, an arbitrary structure or structures may be added.

The medical kit and the liquid filling method may each be a combination of arbitrary two or more configurations (features) of the above embodiment. In addition, while the first syringe assembly has the two syringes connected together in the above embodiment, this is not limitative. The first syringe assembly may have three or more syringes connected to one another. In this case, the numbers of the syringe-side connection portions disposed in the first connector and the second connector are preferably equal to the number of the syringes possessed by the first syringe assembly.

While the second syringe assembly has the two syringes connected together in the above embodiment, this is not restrictive. The second syringe assembly may have three or more syringes connected to one another. Furthermore, while the liquid stored in the liquid storage container is used as a dissolving liquid in the above embodiment, this is not limitative. Where the drugs stored in the first drug storage container and the second drug storage container are liquid, the liquid stored in the liquid storage container may be used as a diluting liquid for diluting the drugs.

The detailed description above describes a medical kit and liquid filling method. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

DESCRIPTION OF REFERENCE SYMBOLS

100 Medical kit
101 First assembly
102 Second assembly
103 Third assembly
10 First syringe assembly (Syringe assembly)
20 Second syringe assembly
30 Regulating mechanism
1*a*, 1*b*, 1*c*, 1*d* Syringe
2 Syringe outer cylinder
21 Barrel portion
211 Distal wall portion
212 Protruding portion
213 Proximal opening portion
22 Mouth portion (Syringe-side mouth portion)
23 Flange portion
3 First connector (Connector)
31 Main body portion
311, 312 Channel
32 Connection portion (Container-side connection portion)
33*a*, 33*b* Connection portion (Syringe-side connection portion)
4 Second connector
41 Main body portion
411, 412 Channel
42*a*, 42*b* Connection portion
43*a*, 43*b* Connection portion
5 Liquid storage container
51 Container main body
52 Mouth portion (Container-side mouth portion)
53 Seal portion
54 Easily breakable portion
6*a* First drug storage container
6*b* Second drug storage container
61 Container main body
62 Mouth portion
63 Plug body
7 Gasket
8 Connection member
81, 82 Plunger portion
811 First engaging portion
812 Locking surface
813 Inclined surface
814 Pressing regulating part
83 Plate-shaped portion (connection portion)
9 Lock member
91 Mounting portion
92 Operation piece
93 Arched portion
94 Second engaging portion
11 Plunger
111, 112 Plunger portion
113 Flange portion
12 Puncture needle
121 Hollow needle
122 Hub
500 Table
P Liquid
Q1, Q2 Drug
R1, R2 Liquid medicine
$t_1$, $t_2$ Thickness
$s_1$, $s_2$ Protrusion amount

What is claimed is:

1. A medical kit comprising:

one liquid storage container including a flexible container main body preliminarily storing a liquid therein, and a container-side mouth portion which communicates with the container main body and which is configured to discharge the liquid inside the container main body therethrough;

at least two syringes each including a syringe outer cylinder having a syringe-side mouth portion through which a liquid can flow in and out, and a gasket slidable within the syringe outer cylinder;

a connector including a container-side connection portion to which the container-side mouth portion is connected in a liquid-tight manner, and syringe-side connection portions which communicate with the container-side connection portion and to which the syringe-side mouth portions are individually connected in a liquid-tight manner; and a regulating mechanism collectively regulating limits of movement of the gaskets toward a side opposite to the container-side mouth portion, wherein the syringes are collectively filled with the liquid by conducting an operation to feed the liquid in the liquid storage container from the liquid storage container side to the syringe side in a condition in which the liquid storage container and the syringes in an unused state of being not yet filled with liquid are connected to each other through the connector, the operation being performed until the regulated limits of movement are reached.

2. The medical kit according to claim 1, wherein the liquid feeding operation is performed by pressing the container main body.

3. The medical kit according to claim 1, wherein the regulating mechanism has a connection member connecting the gaskets to each other, and a majority portion of the connection member is inserted in the syringe outer cylinders in the unused state.

4. The medical kit according to claim 2, wherein the regulating mechanism has a connection member connecting the gaskets to each other, and a majority portion of the connection member is inserted in the syringe outer cylinders in the unused state.

5. The medical kit according to claim 3, wherein the regulating mechanism includes a first engaging portion provided in one of the connection member and the syringe outer cylinder, and a second engaging portion which is provided in an other of the connection member and the syringe outer cylinder and engages with the first engaging portion at the limit of movement.

6. The medical kit according to claim 4, wherein the regulating mechanism includes a first engaging portion provided in one of the connection member and the syringe outer cylinder, and a second engaging portion which is provided in an other of the connection member and the syringe outer cylinder and engages with the first engaging portion at the limit of movement.

7. The medical kit according to claim 3, wherein the first engaging portion is composed of a cutout formed by cutting out in the connection member, and the second engaging portion is composed of a projecting piece projecting from the syringe outer cylinder.

8. The medical kit according to claim 4, wherein the first engaging portion is composed of a cutout formed by cutting out in the connection member, and the second engaging portion is composed of a projecting piece projecting from the syringe outer cylinder.

9. The medical kit according to claim 5, wherein the first engaging portion is composed of a cutout formed by cutting out in the connection member, and the second engaging portion is composed of a projecting piece projecting from the syringe outer cylinder.

10. The medical kit according to claim 6, wherein the first engaging portion is composed of a cutout formed by cutting out in the connection member, and the second engaging portion is composed of a projecting piece projecting from the syringe outer cylinder.

11. The medical kit according to claim 5, wherein engagement between the first engaging portion and the second engaging portion can be cancelled, and the regulating mechanism has an operation section for a cancelling operation to cancel the engagement.

12. The medical kit according to claim 7, wherein engagement between the first engaging portion and the second engaging portion can be cancelled, and the regulating mechanism has an operation section for a cancelling operation to cancel the engagement.

13. The medical kit according to claim 1, wherein the regulating mechanism is configured to maintain the state of the limits of movement.

14. The medical kit according to claim 1, wherein the syringe outer cylinders differ from one another in size.

15. The medical kit according to claim 1, wherein the syringes constitute a syringe assembly in which they are connected to one another.

16. The medical kit according to claim 1, wherein the container-side connection portion and each of the syringe-side connection portions are tubular portions protruding in opposite directions.

17. The medical kit according to claim 1, wherein the liquid is a dissolving liquid or a diluting liquid.

18. A method of filling a liquid into syringes in an unused state of being not yet filled with liquid, the method performed by use of:

one liquid storage container including a flexible container main body preliminarily storing a liquid therein, and a container-side mouth portion which communicates with the container main body and which is configured to discharge the liquid inside the container main body therethrough;

at least two syringes each including a syringe outer cylinder having a syringe-side mouth portion through which a liquid can flow in and out, and a gasket slidable within the syringe outer cylinder;

a connector including a container-side connection portion to which the container-side mouth portion is connected in a liquid-tight manner, and syringe-side connection portions which communicate with the container-side connection portion and to which the syringe-side mouth portions are individually connected in a liquid-tight manner; and a regulating mechanism collectively regulating limits of movement of the gaskets toward a side opposite to the container-side mouth portion, wherein the method comprises filling the liquid into the syringes collectively by conducting an operation to feed the liquid in the liquid storage container from the liquid storage container side to the syringe side in a condition in which the liquid storage container and the syringes in the unused state are connected to each other through the connector, the operation being performed until the regulated limits of movement are reached.

19. The method according to claim 18, wherein the liquid feeding operation is performed by pressing the container main body.

* * * * *